United States Patent
Wijgergangs et al.

(10) Patent No.: US 9,820,973 B2
(45) Date of Patent: Nov. 21, 2017

(54) PHARMACEUTICAL FORMULATION COMPRISING LOSARTAN POTASSIUM AND CHLORTHALIDONE

(71) Applicant: Merck Sharp & Dohme B.V., Rahway, NJ (US)

(72) Inventors: Jan-Piet Wijgergangs, Berghem (NL); Jocominus Antonius Maria Zwinkels, Nistelrode (NL); Albert Falivene Aldea, Barcelona (ES)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/039,262

(22) PCT Filed: Nov. 24, 2014

(86) PCT No.: PCT/EP2014/075371
§ 371 (c)(1),
(2) Date: May 25, 2016

(87) PCT Pub. No.: WO2015/078804
PCT Pub. Date: Jun. 4, 2015

(65) Prior Publication Data
US 2017/0157094 A1  Jun. 8, 2017

(30) Foreign Application Priority Data
Nov. 28, 2013 (EP) .................... 13194786

(51) Int. Cl.
A61K 31/4178  (2006.01)
A61K 31/4035  (2006.01)
A61K 9/20  (2006.01)
A61K 9/28  (2006.01)

(52) U.S. Cl.
CPC ........ *A61K 31/4178* (2013.01); *A61K 9/2009* (2013.01); *A61K 9/2013* (2013.01); *A61K 9/2018* (2013.01); *A61K 9/2027* (2013.01); *A61K 9/2054* (2013.01); *A61K 9/28* (2013.01); *A61K 31/4035* (2013.01)

(58) Field of Classification Search
None
See application file for complete search history.

(56) References Cited

U.S. PATENT DOCUMENTS

2007/0160665 A1* 7/2007 Brand .................... A61K 9/209
424/464

FOREIGN PATENT DOCUMENTS

WO  2009084040 A1  7/2009

OTHER PUBLICATIONS

European Search Report for 13194786.3 dated Apr. 24, 2014, 7 pages.
International Search Report and Written Opinion for PCT/EP2014/075371 dated Feb. 10, 2015, 12 pages.
Jaimini, M et al., International Current Pharmaceutical Journal, Formulation and characterization of gastroretentive drug delivery system of losartan potassium, Jan. 1, 2012, 11-17, 2(1).

* cited by examiner

*Primary Examiner* — Savitha Rao
(74) *Attorney, Agent, or Firm* — Catherine D. Fitch; Richard S. Parr

(57) ABSTRACT

The invention is a pharmaceutical tablet formulation comprising between about 12.5 mg and 100 mg losartan potassium, between about 6.25 mg and about 50 mg chlorthalidone, and sodium bicarbonate in an amount between about 1.0% and about 10.0% by weight.

6 Claims, No Drawings

PHARMACEUTICAL FORMULATION COMPRISING LOSARTAN POTASSIUM AND CHLORTHALIDONE

CROSS REFERENCE TO RELATED APPLICATIONS

This application is a U.S. National Phase application under 35 U.S.C. §371 of PCT Application No. PCT/EP14/075371 filed Nov. 24, 2014, which claims priority from European Patent Application No. 13194786.3, filed Nov. 28, 2013.

BACKGROUND OF THE INVENTION

Losartan potassium is blood pressure reducing angiotensin receptor blocker which is commercially available in tablet forms as a single active ingredient medication (COZAAR®) and also in combination with the diuretic hydrochlorothiazide (HYZAAR®). These tablets are formulated with partially pre-gelatinized corn starch, the function of which is to act as the tablet disintegrant facilitating active ingredient gastric release.

Losartan potassium readily dissolves in neutral to basic media. However, in acidic media, the salt dissociates and the losartan free acid precipitates as a gel layer around the tablet. The gel layer can result in insufficient tablet disintegration of immediate release tablets containing losartan potassium and chlorthalidone, and therefore, insufficient active ingredient release. In order to meet immediate release criteria, effective tablet disintegration in the acidic gastric environment is essential for chlorthalidone, since chlorthalidone has low solubility across the physiologic pH range.

SUMMARY OF THE INVENTION

The invention is a pharmaceutical tablet formulation comprising active ingredients losartan, or a pharmaceutically acceptable salt thereof, and chlorthalidone, and a gas forming disintegrant in amount sufficient to release therapeutically effective amounts of chlorthalidone into the gastric environment. In one embodiment, the gas forming disintegrant is a carbonate salt which generates $CO_2$ gas in the gastric environment, and the losartan salt is losartan potassium. In another embodiment, the carbonate salt is selected from the group consisting of sodium bicarbonate ($NaHCO_3$), sodium carbonate, magnesium carbonate, potassium carbonate, and calcium carbonate. In a further embodiment, the carbonate salt is sodium bicarbonate.

DETAILED DESCRIPTION OF THE DISCLOSURE

The invention is a pharmaceutical tablet formulation comprising active ingredients losartan potassium and chlorthalidone, and sodium bicarbonate, wherein the amount of sodium bicarbonate is between about 1.0% and about 10.0%. Sodium bicarbonate is a required disintegrant for formulations containing losartan potassium and chlorthalidone. Sodium bicarbonate releases carbon dioxide gas which causes the gel layer formed by precipitating losartan free acid in acidic media to break up, allowing complete tablet disintegration and active ingredient release under gastric conditions. The tablets comprise between about 12.5 mg and 100 mg losartan potassium and between about 6.25 mg and about 50 mg chlorthalidone.

The invention is a pharmaceutical tablet formulation comprising between about 12.5 mg and about 100 mg losartan potassium, between about 6.25 mg and about 50 mg chlorthalidone, and sodium bicarbonate in an amount between about 1.0% and about 10.0% by weight.

In one embodiment of the invention, the amount of sodium bicarbonate is between about 3.75 mg and about 37.5 mg.

In another embodiment of the invention, the amount of losartan potassium is 12.5 mg, 25 mg, 50 mg or 100 mg, the amount of chlorthalidone is 6.25 mg, 12.5 mg, 25 mg, or 50 mg, and the amount of sodium bicarbonate is between about 2.0% and 6.0% by weight.

In another embodiment of the invention, the amount of losartan potassium is 12.5 mg, 25 mg, 50 mg or 100 mg, the amount of chlorthalidone is 6.25 mg, 12.5 mg, 25 mg, or 50 mg, and the amount of sodium bicarbonate is between about 7.5 mg and about 22.5 mg.

In another embodiment of the invention, the amount of losartan potassium is 100 mg, the amount of chlorthalidone is 25 mg, and the amount of sodium bicarbonate is about 2.5%. by weight.

In another embodiment of the invention, the amount of losartan potassium is 100 mg, the amount of chlorthalidone is 25 mg, and the amount of sodium bicarbonate is about 9.38 mg.

In another embodiment of the invention, the amount of losartan potassium is 100 mg, the amount of chlorthalidone is 12.5 mg, and the amount of sodium bicarbonate is about 5.0% by weight.

In another embodiment of the invention, the amount of losartan potassium is 100 mg, the amount of chlorthalidone is 12.5 mg, and the amount of sodium bicarbonate is about 18.75 mg.

Another embodiment of the invention is a method for preparing a tablet comprising losartan potassium, chlorthalidone and sodium bicarbonate, comprising blending losartan potassium, chlorthalidone and deagglomerated sodium bicarbonate for form a blend, and compressing the blend to form a compressed tablet.

In one embodiment of the method, the amount of sodium bicarbonate is between about 1.0% and about 10.0% by weight.

The angiotensin II receptor antagonist losartan is described in U.S. Pat. No. 5,136,069, which generically and specifically describes 2-butyl-4-chloro-1-[p-(o-1H-tetrazol-5-ylphenyl)-benzyl]imidazole-5-methanol (losartan) and salts thereof, e.g., sodium or potassium salts, preferably potassium salt (losartan potassium). Columns 261-263 of U.S. Pat. No. 5,136,069 describe general procedures for formulating compounds described in the patent, including capsules, tablets, injection formulations, and suspensions. U.S. Pat. No. 5,153,197, describes the use of these compounds, alone and in combination with a diuretic, to treat a patient having hypertension. Suitable dosing of losartan potassium can be achieved by administering ordinary recommended doses at commercially available strengths, e.g., tablets containing amounts of 25, 50 or 100 mg.

The diuretic chlorthalidone ((RS)-2-chloro-5-(1-hydroxy-3-oxo-2,3-dihydro-1H-isoindol-1-yl)benzene-1-sulfonamide) is a diuretic drug used to treat hypertension, originally marketed as HYGROTON. It is described as a thiazide diuretic (or, rather, a thiazide-like diuretic because it acts similarly to the thiazides but does not contain the benzothiadiazine molecular structure). Compared with other medications of the thiazide class, chlorthalidone has the longest duration of action but a similar diuretic effect at maximal therapeutic doses. It is often used in the management of hypertension and edema.

Chlorthalidone increases the excretion of sodium, chloride, and water into the renal lumen by inhibiting sodium ion transport across the renal tubular epithelium. Its primary site of action is in the cortical diluting segment of the ascending limb of the loop of Henle. Thiazides and related compounds also decrease the glomerular filtration rate, which further reduces the drug's efficacy in patients with renal impairment (e.g. renal insufficiency). By increasing the delivery of sodium to the distal renal tubule, chlorthalidone indirectly increases potassium excretion via the sodium-potassium exchange mechanism (i.e. apical ROMK/Na channels coupled with basolateral NKATPases). This can result in hypokalemia and hypochloremia as well as a mild metabolic alkalosis; however, the diuretic efficacy of chlortalidone is not affected by the acid-base balance of the patient being treated.

The term "a gas forming disintegrant in amount sufficient to release therapeutically effective amounts of chlorthalidone into the gastric environment" means an amount that generates the release of chlorthalidone and results in therapeutically meaningful lowering of blood pressure in a patient. Therapeutically meaningful lowering of blood pressure is associated with at least 25% release of a 25 mg dose of chlorthalidone within 15 minutes of ingestion, at least 45% release of a 25 mg dose of chlorthalidone within 30 minutes of ingestion, at least 54% release of a 25 mg dose of chlorthalidone within 45 minutes of ingestion, or at least 61% release of a 25 mg dose of chlorthalidone within 60 minutes of ingestion.

Suitable dosing of chlorthalidone can be achieved by administering ordinary recommended doses at commercially available strengths, e.g., tablets containing amounts of 15, 25, or 50 mg.

The compositions of the present invention may also comprise suitable fillers, binders, glidants, lubricants and other disintegrants.

Examples of fillers (also referred to as bulking agents or diluents) suitable for use herein include, but are not limited to, cellulose derivatives, such as microcrystalline cellulose or wood cellulose (including microcrystalline cellulose 302), lactose, lactose anhydrous, sucrose, starch, pregelatinized starch, dextrose, mannitol (including mannitol Pearlitol SD 200), fructose, xylitol, sorbitol, corn starch, modified corn starch, inorganic salts such as calcium carbonate, calcium phosphate, dicalcium phosphate, calcium sulfate, dextrin/dextrates, maltodextrin, compressible sugars, and other known bulking agents or fillers, and/or mixtures of two or more thereof. Several types of microcrystalline cellulose are suitable for use in the formulations described herein, for example, microcrystalline cellulose selected from the group consisting of Avicel® types: PH101, PH102, PH103, PH105, PH 112, PHI 13, PH200, PH301, and other types of microcrystalline cellulose, such as silicified microcrystalline cellulose. Several types of lactose are suitable for use in the formulations described herein, for example, lactose selected from the group consisting of anhydrous lactose, lactose monohydrate, lactose fast flo, directly compressible anhydrous lactose, and modified lactose monohydrate.

Examples of binders suitable for use herein include, but are not limited to, carboxymethyl cellulose (including sodium carboxymethyl cellulose), hydroxypropyl cellulose (including hydroxypropyl cellulose EXF), corn starch, pregelatinized starch, modified corn starch, polyvinyl pyrrolidone (PVP), hydroxypropyl methylcellulose (HPMC) (including hydroxypropyl methylcellulose 2208), lactose, gum acacia, ethyl cellulose, cellulose acetate, as well as a wax binder such as carnauba wax, paraffin, spermaceti, polyethylenes or microcrystalline wax, as well as other conventional binding agents and/or mixtures of two or more thereof.

Examples of glidants and/or anti-adherents suitable for use herein include but are not limited to, silicon dioxide, colloidal silicon dioxide, magnesium silicate, magnesium trisilicate, talc, and other forms of silicon dioxide, such as aggregated silicates and hydrated silica. Examples of suitable release modifiers include, but are not limited to, hydroxypropyl methylcellulose, polyvinyl alcohol (PVA), ethyl cellulose, methacrylic polymers, hydroxypropyl cellulose, starches, gums, cellulose ethers, protein derived materials, nylon, acrylic resins, polylactic acid, polyvinylchloride, polyvinylpyrrolidones, and cellulose acetate phthalate.

Examples of lubricants suitable for use herein include, but are not limited to, magnesium stearate, zinc stearate, calcium stearate, talc, carnauba wax, stearic acid, palmitic acid, sodium stearyl fumarate, sodium laurel sulfate, glyceryl palmitostearate, myristic acid, hydroxypropyl methylcellulose, and hydrogenated vegetable oils and fats, as well as other known lubricants, and/or mixtures of two or more thereof.

Disintegrants which are suitable for the present invention are gas forming carbonate disintegrants which generate $CO_2$ gas in the gastric environment. Such disintegrants are sodium bicarbonate, sodium carbonate, magnesium carbonate, potassium carbonate, and calcium carbonate. Sodium bicarbonate is the preferred carbonate.

Examples of other disintegrants suitable for use herein in combination with gas forming disintegrants include, but are not limited to, croscarmellose sodium, crospovidone, starch, potato starch, pregelatinized starch, corn starch, sodium starch glycolate, microcrystalline cellulose, low substituted hydroxypropyl cellulose and other known disintegrants. Several specific types of disintegrant are suitable for use in the formulations described herein. For example, any grade of crospovidone can be used, including for example crospovidone XL-10, and includes members selected from the group consisting of Kollidon CL®, Polyplasdone XL®, Kollidon CL-M®, Polyplasdone XL-10®, and Polyplasdone INF-10®. In particular, disintegrants such as crospovidone, which swell by absorption of water, are suitable in the presence of sodium bicarbonate.

Example 1

The following tablet was prepared.

| | | Uncoated tablet | |
|---|---|---|---|
| % w/w | Unit Formula (mg) | Ingredient | Function |
| 26.6667 | 100.00 | Losartan Potassium | active |
| 3.33333 | 12.50 | Chlorthalidone | active |
| 37.6667 | 141.25 | Microcrystalline Cellulose | compression aid/diluent |
| 18.8333 | 70.63 | Lactose Monohydrate | diluent |
| 6 | 22.50 | Crospovidone | disintegrant |
| 5 | 18.75 | Sodium Bicarbonate | disintegrant |
| 2.5 | 9.38 | Sodium Stearyl Fumarate | lubricant |
| 100 | 375 | Total | |

Coating Suspension

| % w/w | Unit Formula (mg) | Ingredient | Function |
|---|---|---|---|
| 3 | 11.25 | Opadry II (85F92209 YELLOW) | colorant |
| 3 | 11.25 | Total | |

Preparation

Crospovidone, lactose, chlorthalidone, losartan potassium, deagglomerated sodium bicarbonate and a portion of microcrystalline cellulose are blended together to form a first blend. A remaining portion of microcrystalline cellulose and sodium stearyl fumarate are blended and deagglomerated and subsequently added to the first blend, and then blended and compressed to form a tablet. The tablet is then coated with a suspension of PVA-PEG (e.g., Opadry II) in purified water.

Example 2

The following tablet was prepared.

Uncoated tablet

| % w/w | Unit Formula (mg) | Ingredient | Function |
|---|---|---|---|
| 26.6667 | 100.00 | Losartan Potassium | active |
| 6.67 | 25.00 | Chlorthalidone | active |
| 33.4 | 62.71 | Microcrystalline Cellulose | compression aid/diluent |
| 5.00 | 18.75 | Lactose Monohydrate | diluent |
| 9.00 | 33.75 | Crospovidone | disintegrant |
| 2.50 | 9.38 | Sodium Bicarbonate | disintegrant |
| 6.67 | 25.00 | Sodium Stearyl Fumarate | lubricant |
| 100 | 375 | Total | |

Coating Suspension

| % w/w | Unit Formula (mg) | Ingredient | Function |
|---|---|---|---|
| 3 | 11.25 | Opadry II (85F92209 YELLOW) | colorant |
| 3 | 11.25 | Total | |

Preparation

Crospovidone, Lactose, chlorthalidone, Losartan potassium, deagglomerated sodium bicarbonate and a portion of microcrystalline cellulose are blended together to form a first blend. A remaining portion of microcrystalline cellulose and sodium stearyl fumarate are blended and deagglomerated and subsequently added to the first blend, and then blended and compressed to form a tablet. The tablet is then coated with a suspension of PVA-PEG (e.g., Opadry II) in purified water.

Example 3

To compare the effect of the presence of sodium bicarbonate on release of chlorthalidone, two formulations were prepared according to the general procedures described in Examples 1 and 2.

The first formulation (3-1) contained no sodium bicarbonate:

Formulation 3-1

| % w/w | Unit Formula (mg) | Ingredient |
|---|---|---|
| 22.2222 | 50 | Losartan Potassium |
| 11.1111 | 25 | Chlorthalidone |
| 24.2667 | 54.6 | Microcrystalline Cellulose |
| 36.4 | 81.9 | Lactose Monohydrate |
| 5 | 11.25 | Crospovidone |
| 1 | 2.25 | Magnesium Stearate |
| 100 | 225 | Total |

The second formulation (3-2) contained 5% sodium bicarbonate:

Formulation 3-2

| % w/w | Unit Formula (mg) | Ingredient |
|---|---|---|
| 22.22 | 50.00 | Losartan Potassium |
| 11.11 | 25.00 | Chlorthalidone |
| 26.99 | 60.72 | Microcrystalline Cellulose |
| 26.99 | 60.72 | Lactose Monohydrate |
| 5.00 | 11.25 | $NaHCO_3$ |
| 7.00 | 15.75 | Crospovidone |
| 0.70 | 1.58 | Magnesium Stearate |
| 100 | 225 | Total |

Under simulated gastric conditions (250 ml SGF (20 g/L NaCl, 0.017M HCl, pH=1.8)), the presence of sodium bicarbonate resulted in release of chlorthalidone. Chlorthalidone was not effectively released in the absence of sodium bicarbonate.

Release % of Chlorthalidone in Simulated Gastric Conditions

| Time (min) | Formulation 3-1 (No $NaHCO_3$) | Formulation 3-2 5% $NaHCO_3$ |
|---|---|---|
| 0 | 0% | 0% |
| 5 | 1% | 16% |
| 10 | 2% | 39% |
| 15 | 3% | 54% |
| 30 | 8% | 74% |
| 45 | 12% | 82% |
| 60 | 17% | 86% |

Example 4

To compare the effect of various levels of sodium bicarbonate on the release of chlorthalidone, three formulations, with 2.5% (4-1), 5% (4-2) or 7.5% (4-3) sodium bicarbonate, were prepared according to the general procedures described in Examples 1 and 2.

| Ingredient | 2.5% $NaHCO_3$ (4-1) | 5% $NaHCO_3$ (4-2) | 7.5% $NaHCO_3$ (4-3) |
|---|---|---|---|
| Losartan Potassium | 100.0 | 100.0 | 100.0 |
| Chlorthalidone | 25.0 | 25.0 | 25.0 |
| Crospovidone | 22.5 | 22.5 | 22.5 |

-continued

| Ingredient | 2.5% NaHCO₃ (4-1) | 5% NaHCO₃ (4-2) | 7.5% NaHCO₃ (4-3) |
| --- | --- | --- | --- |
| Lactose Monohydrate | 69.6 | 66.5 | 63.3 |
| NaHCO3 | 9.3 | 18.8 | 28.2 |
| Micro crystalline cellulose | 139.2 | 132.9 | 126.6 |
| Sodium stearyl fumarate | 9.4 | 9.4 | 9.4 |
| Total mass (mg): | 375.0 | 375.0 | 375.0 |

Dissolution results in 900 ml buffer pH1.2 showed the following amounts of release of chlorthalidone.

% Chlorthalidone release over time

| Time | 2.5%_NaHCO₃ (4-1) | 5% NaHCO₃ (4-2) | 7.5%_NaHCO₃ (4-3) |
| --- | --- | --- | --- |
| 15 | 25% | 41% | 54% |
| 30 | 45% | 73% | 82% |
| 45 | 53% | 82% | 88% |
| 60 | 60% | 85% | 91% |

Results show that 2.5% sodium bicarbonate provides significant chlorthalidone release, and that 5% and 7.5% provide nearly complete release of chlorthalidone.

Example 5

Dissolution of losartan potassium (COZAAR® 50 mg), which employs pregelatinized starch as the disintegrant, was compared to dissolution of chlorthalidone formulated in the same tablet composition (5-1). The study showed that dissolution of chlorthalidone was significantly lower than dissolution of losartan potassium.

Composition of Example 5-1

| % w/w | Unit formula (mg) | Ingredient |
| --- | --- | --- |
| 22.22 | 50.0 | Losartan Potassium |
| 11.11 | 25.0 | Chlorthalidone |
| 12.13 | 27.3 | Microcrystalline cellulose |
| 36.40 | 81.9 | Lactose Mono hydrate |
| 4.00 | 11.25 | Crospovidone |
| 12.13 | 27.3 | Pregelatinized starch |
| 1.00 | 2.25 | Magnesium Stearate |

Dissolution Results

| Dissolution of COZAAR ® 50 mg in 900 ml of 0.01N HCl | | Dissolution of Example 5-1 in 250 ml of SGF |
| --- | --- | --- |
| Time (min) | % Dissolved Losartan Potassium | % Dissolved Chlorthalidone |
| 0.0 | 0 | 0 |
| 5.0 | 0.3 | 1.1 |
| 10.0 | 0.8 | 3.2 |
| 15.0 | 1.6 | 5.5 |
| 30.0 | 3.9 | 12.5 |
| 45.0 | 8.6 | 18.6 |
| 60.0 | 18.9 | 22.7 |

The above data show that COZAAR® 50 mg tablets do not dissolve well in acidic environment. Despite that fact, the formulation delivers therapeutically effective levels of losartan potassium to the patient.

The data also show that a modified disintegrant system, used in Example 5-1, employing both pregelatinized starch and crospovidone does not significantly improve dissolution in acidic environment. Because chlorthalidone has low solubility across the physiologic pH range, this shows that the modified disintegrant system does not result in chlorthalidone dissolution in acidic environment sufficient to deliver therapeutically effective levels of chlorthalidone.

What is claimed is:

1. A pharmaceutical tablet formulation comprising an amount of losartan potassium which is 12.5 mg, 25 mg, 50 mg or 100 mg, an amount of chlorthalidone which is 6.25 mg, 12.5 mg, 25 mg, or 50 mg, and an amount of sodium bicarbonate which is between about 2.0% and 6.0% by weight.

2. The formulation of claim 1, wherein the amount of losartan potassium is 12.5 mg, 25 mg, 50 mg or 100 mg, the amount of chlorthalidone is 6.25 mg, 12.5 mg, 25 mg, or 50 mg, and the amount of sodium bicarbonate is between about 7.5 mg and about 22.5 mg.

3. The formulation of claim 1, wherein the amount of losartan potassium is 100 mg, the amount of chlorthalidone is 25 mg, and the amount of sodium bicarbonate is about 2.5% by weight.

4. The formulation of claim 2, wherein the amount of losartan potassium is 100 mg, the amount of chlorthalidone is 25 mg, and the amount of sodium bicarbonate is about 9.38 mg.

5. The formulation of claim 1, wherein the amount of losartan potassium is 100 mg, the amount of chlorthalidone is 12.5 mg, and the amount of sodium bicarbonate is about 5.0% by weight.

6. The formulation of claim 2, wherein the amount of losartan potassium is 100 mg, the amount of chlorthalidone is 12.5 mg, and the amount of sodium bicarbonate is about 18.75 mg.

* * * * *